United States Patent
Dorros et al.

(10) Patent No.: US 6,855,136 B2
(45) Date of Patent: Feb. 15, 2005

(54) INFUSION CATHETER HAVING AN ATRAUMATIC TIP

(75) Inventors: Gerald Dorros, Scottsdale, AZ (US); Michael Hogendijk, Palo Alto, CA (US); Mark C. Bates, Charleston, WV (US)

(73) Assignee: Gore Enterprise Holdings, Inc., Newark, DE (US)

( * ) Notice: Subject to any disclaimer, the term of this patent is extended or adjusted under 35 U.S.C. 154(b) by 0 days.

(21) Appl. No.: 10/134,237

(22) Filed: Apr. 25, 2002

(65) Prior Publication Data

US 2003/0191434 A1 Oct. 9, 2003

Related U.S. Application Data

(60) Provisional application No. 60/370,040, filed on Apr. 3, 2002.

(51) Int. Cl.[7] .............................................. A61M 31/00
(52) U.S. Cl. .................. 604/508; 604/6.09; 604/96.01; 604/523; 604/264; 604/151; 604/528; 604/529; 604/131
(58) Field of Search ..................... 604/96.01, 101.01, 604/101.03, 101.04, 506–510, 104, 105, 164.13, 265, 529, 266, 523, 915, 264, 93.01, 524; 606/192, 194, 198

(56) References Cited

U.S. PATENT DOCUMENTS

| | | | |
|---|---|---|---|
| 4,464,176 A | | 8/1984 | Wijayarathna |
| 4,661,094 A | | 4/1987 | Simpson |
| 4,968,306 A | * | 11/1990 | Huss et al. ................. 604/264 |
| 5,180,387 A | | 1/1993 | Ghajar et al. |
| 5,184,627 A | | 2/1993 | de Toledo |
| 5,211,636 A | | 5/1993 | Mische |
| 5,376,083 A | | 12/1994 | Mische |
| 5,380,307 A | * | 1/1995 | Chee et al. ................. 604/264 |

(List continued on next page.)

*Primary Examiner*—Nicholas D. Lucchesi
*Assistant Examiner*—Cris L. Rodriguez
(74) *Attorney, Agent, or Firm*—Kevin J. Boland

(57) ABSTRACT

The present invention is directed to apparatus and methods for treating a vascular occlusion by providing an infusion catheter having an atraumatic tip and at least one delivery port configured to infuse fluid into the occlusion. The fluid that is infused dilutes the occlusion and reduces adhesion of the occlusion to an intima of the vessel wall, thereby causing the occlusion to dislodge. Emboli generated in the process are directed into an emboli removal catheter for removal.

35 Claims, 2 Drawing Sheets

U.S. PATENT DOCUMENTS

| | | | |
|---|---|---|---|
| 5,554,114 A * | 9/1996 | Wallace et al. | 604/508 |
| 5,569,197 A | 10/1996 | Helmus et al. | |
| 5,609,574 A | 3/1997 | Kaplan et al. | |
| 5,624,396 A | 4/1997 | McNamara et al. | |
| 5,643,228 A | 7/1997 | Schucart et al. | |
| 5,702,372 A | 12/1997 | Nelson | |
| 5,713,860 A | 2/1998 | Kaplan et al. | |
| 5,782,797 A | 7/1998 | Schweich, Jr. et al. | |
| 5,800,408 A | 9/1998 | Strauss et al. | |
| 5,947,985 A * | 9/1999 | Imran | 606/159 |
| 5,972,019 A * | 10/1999 | Engelson et al. | 606/200 |
| 5,997,487 A | 12/1999 | Kolehmainen et al. | |
| 6,004,279 A * | 12/1999 | Crowley et al. | 600/585 |
| 6,022,336 A * | 2/2000 | Zadno-Azizi et al. | 604/101.05 |
| 6,027,461 A | 2/2000 | Walker et al. | |
| 6,059,745 A | 5/2000 | Gelbfish | |
| 6,059,760 A | 5/2000 | Sandmore et al. | |
| 6,063,069 A * | 5/2000 | Cragg et al. | 604/508 |
| 6,102,903 A | 8/2000 | Tremulis | |
| 6,117,125 A * | 9/2000 | Rothbarth et al. | 604/523 |
| 6,179,813 B1 * | 1/2001 | Ballow et al. | 604/164.01 |
| 6,179,816 B1 * | 1/2001 | Mottola et al. | 604/264 |
| 6,283,947 B1 | 9/2001 | Mirzaee | |
| 6,295,990 B1 * | 10/2001 | Lewis et al. | 128/898 |
| 6,302,990 B1 | 10/2001 | Nelson | |
| 6,527,979 B2 * | 3/2003 | Constantz et al. | 252/364 |
| 6,533,763 B1 * | 3/2003 | Schneiter | 604/264 |
| 6,533,767 B2 * | 3/2003 | Johansson et al. | 604/507 |
| 2002/0010487 A1 * | 1/2002 | Evans et al. | 606/180 |
| 2002/0062119 A1 * | 5/2002 | Zadno-Azizi | 604/509 |
| 2003/0023227 A1 * | 1/2003 | Zadno-Azizi et al. | 604/509 |
| 2003/0040705 A1 * | 2/2003 | Dorros et al. | 604/102.02 |
| 2003/0097094 A1 * | 5/2003 | Ouriel et al. | 604/93.01 |

* cited by examiner

INFUSION CATHETER HAVING AN ATRAUMATIC TIP

CROSS REFERENCE TO RELATED APPLICATIONS

This application claims the benefit of U.S. provisional application Ser. No. 60/370,040, filed Apr. 3, 2002.

FILED OF THE INVENTION

The present invention relates to apparatus and methods for treating a vascular occlusion, and more specifically, treating the occlusion by providing an infusion catheter having an atraumatic tip and at least one delivery port configured to infuse fluids into the occlusion and dislodge the occlusion.

BACKGROUND OF THE INVENTION

Intravascular occlusions requiring intervention may be treated using a variety of known medical techniques. In each of these techniques, it is desirable to provide a retrograde flow potential at the treatment site. This causes emboli that are liberated during treatment to flow in a proximal direction, so that the emboli do not travel deeper into the vascular bed and cause further occlusive events resulting in infarction and/or necrosis.

A commonly known technique for treating a vascular occlusion involves delivering lytic agents to the site of the occlusion to dissolve the occlusion. One drawback associated with such lytic agents is that they may facilitate bleeding and/or cause damage to the vessel wall.

Previously known infusion guidewires or catheters have been used to deliver such fluids to a treatment site. For example, U.S. Pat. No. 6,027,461 to Walker et al. (Walker) describes a tubular outer sheath having proximal and distal ends and a lumen extending therebetween, wherein the sheath comprises a plurality of infusion ports disposed in the sheath wall near the distal end. An integral core wire is disposed within the lumen of the outer sheath, and is affixed at a distal tip of the outer sheath to increase pushability of the outer sheath. An annulus formed between an inner wall of the outer sheath and the integral core wire defines an infusion lumen, whereby fluid may be delivered to a vascular treatment site via the infusion lumen and the infusion ports of the outer sheath.

The device described in the Walker patent has several drawbacks. First, the integral core wire, which is affixed within the lumen of the outer sheath, comprises a relatively large profile within the outer sheath, which in turn reduces the infusion lumen area and may hamper fluid transfer to the distal end of the outer sheath. The device is configured to permit the introduction of drugs or lytic agents to a treatment site, however, as noted above, the use of such lytic agents may facilitate bleeding. Additionally, the fluids that exit the infusion ports are infused into the occlusion in a direction that is orthogonal to the outer sheath, which may cause emboli that are liberated during the lytic process to travel in a direction downstream from the occlusion, thereby making them difficult to retrieve from a patient's vessel.

In view of these drawbacks of previously known systems, it would be desirable to provide apparatus and methods for treating a vascular occlusion by infusing fluid into the occlusion to dilute the occlusion and reduce adhesion of the occlusion to the intima of the vessel wall.

It also would be desirable to provide apparatus and methods for treating a vascular occlusion by infusing fluid into the occlusion in a proximal direction so that emboli generated may be urged in the proximal direction.

It further would be desirable to provide apparatus and methods for treating a vascular occlusion that utilize a centering device to assist in positioning and stabilizing an infusion catheter within the occlusion.

SUMMARY OF THE INVENTION

In view of the foregoing, it is an object of the present invention to provide apparatus and methods for treating a vascular occlusion by infusing fluid into the occlusion to dilute the occlusion and reduce adhesion of the occlusion to the intima of the vessel wall.

It is also an object of the present invention to provide apparatus and methods for treating a vascular occlusion by infusing fluid into the occlusion in a proximal direction so that emboli generated may be urged in the proximal direction.

It is a further object of the present invention to provide apparatus and methods for treating a vascular occlusion that utilize a centering device to assist in positioning and stabilizing an infusion catheter within the occlusion.

These and other objects of the present invention are accomplished by providing an infusion catheter having an atraumatic tip disposed at the distal end, and at least one delivery port disposed proximal of the atraumatic tip that is configured to infuse fluid into the occlusion. The fluid that is infused dilutes and/or fragments the occlusion and reduces adhesion of the occlusion to the intima of the vessel wall. This in turn causes the occlusion to dislodge. Emboli generated in the process are directed into an emboli removal catheter for removal via a retrograde flow potential provided by the emboli removal catheter. The delivery port may include an angled taper that directs infused fluid into the occlusion in a proximal direction. Additionally, a centering device may be used in conjunction with the infusion catheter to position and stabilize the infusion catheter within the occlusion.

In a preferred method, the emboli removal catheter is disposed in a patient's vessel proximal of an occlusion, and an occlusive element disposed at the distal end of the emboli removal catheter is deployed to occlude antegrade flow into the treatment vessel. Retrograde flow then may be established through the lumen of the emboli removal catheter, preferably using an arterial-venous shunt, as described hereinbelow. With retrograde flow established in the treatment vessel, the infusion catheter is advanced distally through the emboli removal catheter, and the atraumatic tip of the infusion catheter is advanced through the occlusion.

A physician positions the infusion catheter so that at least one delivery port is disposed within the occlusion, e.g., under fluoroscopy using at least one radiopaque marker band disposed on the infusion catheter. Fluid is infused into the occlusion via the lumen of the infusion catheter and the delivery port. The fluid that is infused, which preferably comprises saline, dilutes the occlusion, which comprises a fibrin network in which red blood cells are trapped. The dilution of the occlusion may change the composition of the occlusion and provide a lubricious coating between the occlusion and the vessel wall, which in effect reduces adhesion of the occlusion to the vessel wall, thus causing the occlusion to dislodge. Emboli generated during this process are carried in a retrograde fashion into the emboli removal catheter due to the established retrograde flow. In a preferred embodiment, the delivery port comprises a taper that causes infused fluid to be directed in a proximal direction so that emboli generated may be urged in the proximal direction, i.e., toward the emboli removal catheter.

In an alternative embodiment, an infusion catheter constructed in accordance with principles of the present invention may be used in conjunction with a centering device having a plurality of deployable struts. The centering device is provided in a contracted state and is disposed proximal of the occlusion. The deployable struts then are deployed to anchor the centering device, and the infusion catheter is guided into a central portion of the occlusion via the centering device.

BRIEF DESCRIPTION OF THE DRAWINGS

Further features of the invention, its nature and various advantages will be more apparent from the accompanying drawings and the following detailed description of the preferred embodiments, in which.

DETAILED DESCRIPTION OF THE INVENTION

The present invention is directed to apparatus and methods for treating a vascular occlusion by providing an infusion catheter having an atraumatic tip and at least one delivery port configured to infuse fluid into the occlusion. The fluid that is infused dilutes the occlusion and reduces adhesion of the occlusion to the intima of the vessel wall, thereby causing the occlusion to dislodge. Emboli generated in the process are directed into an emboli removal catheter for safe removal.

Figure 1:
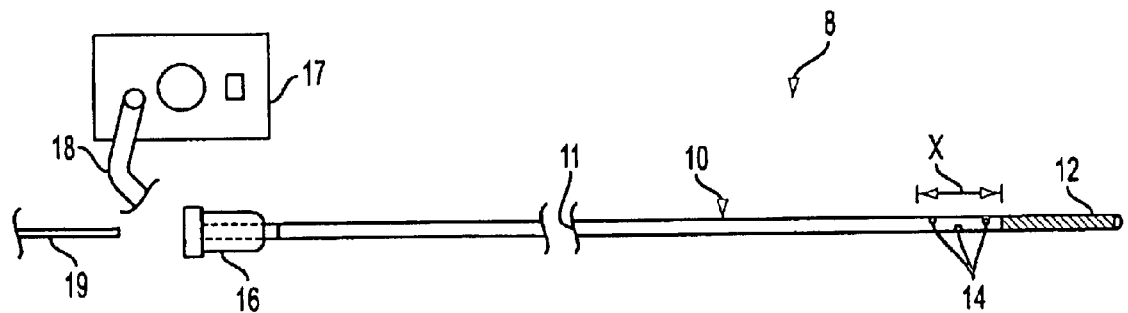
FIG. 1 provides a side view of apparatus constructed in accordance with principles of the present invention.

Referring to FIG. 1, a side view of apparatus constructed in accordance with principles of the present invention is provided. Apparatus 8 of the present invention preferably comprises infusion catheter 10 having proximal and distal ends and lumen 11 extending therebetween. Infusion catheter 10 further comprises atraumatic tip 12 disposed at the distal end. Atraumatic tip 12 preferably comprises a platinum coil so that a physician may navigate a patient's vasculature using the coil and further track the distal end under fluoroscopy.

Infusion catheter 10 preferably is configured to have sufficient axial pushability so that it may cross a lesion without kinking, while being flexible enough to be guided through tortuous vasculature. Removable stylet 19, which is configured to be longitudinally advanced within lumen 11, optionally may be disposed within lumen 11 during insertion of infusion catheter 10 to enhance pushability. Alternatively, as described hereinbelow with respect to FIG. 3, infusion catheter 10 also may be guided to a treatment site using a conventional guidewire in combination with a micro catheter.

Figure 4:
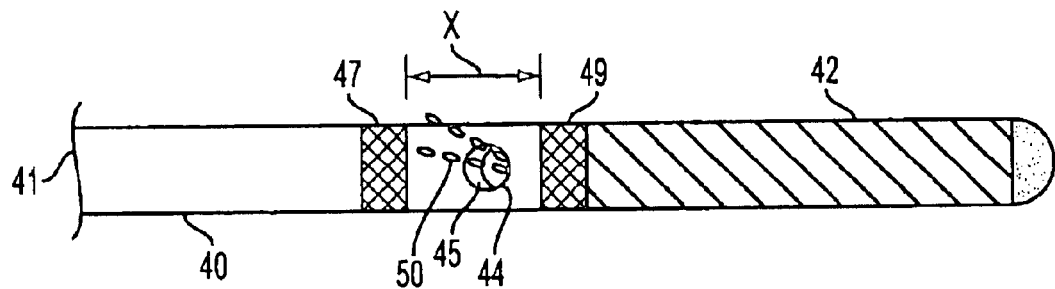
FIG. 4 provides a side view of the distal end of an infusion catheter constructed in accordance with principles of the present invention.

Infusion catheter 10 further comprises at least one delivery port 14 disposed proximal of atraumatic tip 12, as shown in FIG. 1, and more preferably four or more ports spaced circumferentially around infusion catheter 10. Delivery port 14 is in fluid communication with lumen 11 of infusion catheter 10. As described hereinbelow with respect to FIG. 4, delivery port 14 may be angled so that fluid exits delivery port 14 in a proximal direction. Infusion segment 'x' may be defined by a plurality of radiopaque marker bands, as shown in FIG. 4 hereinbelow, that allow a physician to better visualize where delivery port 14 is disposed within an occlusion.

The proximal end of infusion catheter 10 is coupled to proximal hub 16, which preferably comprises a luer fitting that enables fluid communication between an infusion means, e.g., a syringe (not shown), and lumen 11 of infusion catheter 10. Proximal hub 16 alternatively may be coupled to infusion pump 17, which allows fluid to be delivered into lumen 11 at a controlled rate via tubing 18.

Figure 2:
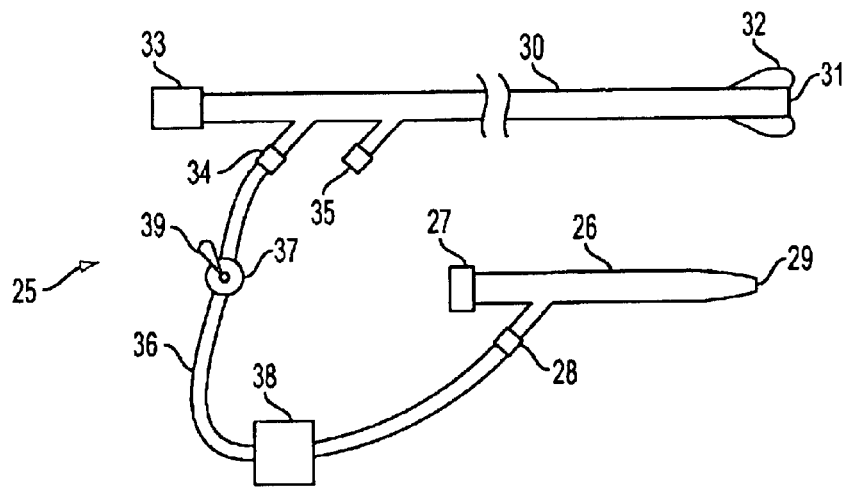
FIG. 2 provides a side view of preferred apparatus for providing a retrograde flow potential in a treatment vessel.

Referring now to FIG. 2, preferred apparatus that may be used in conjunction with apparatus 8 of FIG. 1 to provide retrograde flow potential in a treatment vessel and remove emboli is described. In FIG. 2, embolic protection apparatus 25 preferably comprises emboli removal catheter 30 having proximal and distal ends and lumen 31 extending therebetween, venous return sheath 26, tubing 36 and, optionally, blood filter 38 and/or flow control valve 37.

Emboli removal catheter 30 includes distal occlusive element 32, proximal hemostatic port 33, e.g., a Touhy-Borst connector, inflation port 35, and blood outlet port 34. Tubing 36 couples blood outlet port 34 to flow control valve 37, and also couples flow control valve 37 to filter 38 and blood inlet port 28 of venous return sheath 26. Hemostatic port 33 and lumen 31 of emboli removal catheter 30 are sized to permit the advancement of infusion catheter 10 of FIG. 1.

Venous return sheath 26 includes hemostatic port 27, blood inlet port 28 and a lumen that communicates with ports 27 and 28 and tip 29. Venous return sheath 26 may be constructed in a manner per se known for venous introducer catheters. Tubing 36 may comprise a suitable length of a biocompatible material, such as silicone. Alternatively, tubing 36 may be omitted and blood outlet port 34 of emboli removal catheter 30 and blood inlet port 28 of venous return sheath 26 may be lengthened to engage either end of filter 38, flow control valve 37, or each other. In yet a further alternative embodiment, venous return sheath 26 may be omitted entirely, and a proximal portion of emboli removal catheter 30 may be lengthened so that is adapted to be disposed directly into a patient's venous vasculature. As a yet further alternative, venous return sheath 26 and filter 38 may be omitted. This option may be desirable where a continuous supply of fluid is provided through apparatus 8 at a rate sufficient to cause hemodilution.

In use, emboli removal catheter 30 is advanced over a guide wire (not shown) to a location proximal of an occlusion. Occlusive element 32 then is inflated via inflation port 35, preferably using a radiopaque contrast solution, and the guide wire may be removed. For an occlusion located in a patient's cerebral vasculature, e.g., a mid-cerebral artery, it is preferred that occlusive element 32 be deployed in a patient's common carotid artery (CCA) on the hemisphere of the cerebral occlusion. In this scenario, once occlusive element 32 is deployed in the CCA, flow within the external carotid artery (ECA) reverses and provides antegrade flow into the internal carotid artery (ICA) due to the lower hemodynamic resistance of the ICA.

Venous return sheath 26 then is introduced into the patient's femoral vein, either percutaneously or via a surgical cut-down. Filter 38 and/or flow control valve 37 may be coupled between blood outlet port 34 of emboli removal catheter 30 and blood inlet port 28 of venous return sheath 26 using tubing 36, and any air is removed from the line. Once this circuit is closed, negative pressure in the venous sheath during diastole will establish a low rate continuous flow of blood through lumen 31 of catheter 30, to the patient's vein via venous return sheath 26.

At this time, a low profile balloon (not shown) may be deployed in the ECA to prevent flow from the ECA to be carried in an antegrade fashion into the ICA, e.g., using apparatus and methods described in applicant's commonly assigned, co-pending U.S. patent application Ser. No. 09/972,225. The deployment of the low profile balloon in the ECA, in conjunction with the negative pressure in venous return sheath 26 during diastole, establishes a retrograde flow dynamic in the ICA and selected cerebral locations.

This continuous retrograde flow in the ICA due to the difference between venous pressure and arterial pressure will continue throughout the interventional procedure. Specifically, blood passes through lumen 31 and blood outlet port 34 of emboli removal catheter 30, through biocompatible tubing 36 to flow control valve 37 and/or filter 38, and into blood inlet port 28 of venous return sheath 26, where it is reperfused into the remote vein. Filtered emboli collect in filter 38 and may be studied and characterized upon completion of the procedure. During use, switch 39, which is coupled to flow control valve 37, may be used to selectively inhibit fluid communication between lumen 31 of emboli removal catheter and the lumen of venous return sheath 26.

Figure 3:
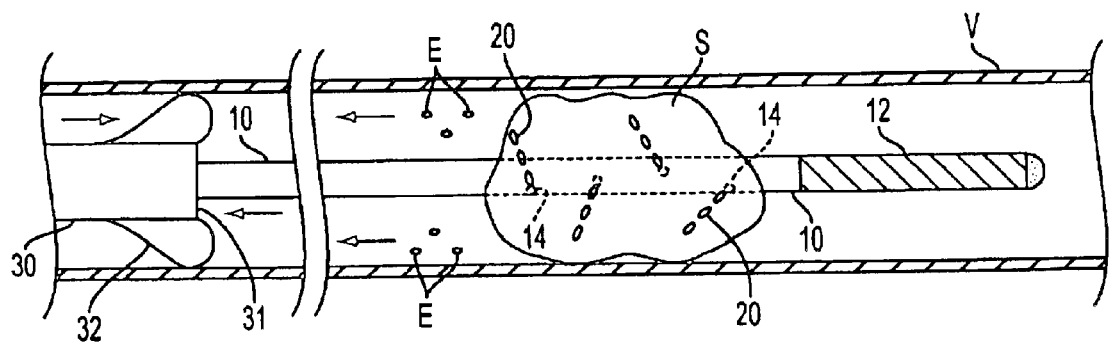
FIG. 3 provides a side sectional view of the device of FIGS. 1–2 being used to treat a vascular occlusion.

Referring to FIG. 3, a method for using apparatus 8 of FIG. 1 to treat a vascular occlusion is described. In a first method step, emboli removal catheter 30 of FIG. 2 may be introduced into a patient's vasculature over a guidewire (not shown) with occlusive element 32 in a contracted state. The distal end of emboli removal catheter 30 then is positioned at a location proximal of occlusion S, and occlusive element 32 is deployed. Occlusive element 32 preferably comprises a balloon, which is deployed via inflation port 35 of FIG. 2. The deployment of occlusive element 32 serves to occlude antegrade flow into vessel V. Retrograde flow is provided through lumen 31 of emboli removal catheter 30, preferably using the natural aspiration techniques described hereinabove with respect to FIG. 2. In this technique, venous return sheath 26 is disposed in a remote vein, and the difference between venous and arterial pressure induces a substantially continuous level of retrograde flow in vessel V. The direction of flow in treatment vessel V is illustrated by the arrows in FIG. 3, which is toward emboli removal catheter 30. For an occlusion S residing in a patient's cerebral vasculature, e.g., a middle cerebral artery, it is preferred that occlusive element 32 is deployed in a patient's common carotid artery.

With controlled flow provided in treatment vessel V, an infusion means, e.g., a syringe (not shown) or, alternatively, tubing 18 of infusion pump 17 of FIG. 1, then is coupled to proximal hub 16. The infusion means preferably supplies saline, but alternatively may supply lytic agents. With the infusion means coupled to proximal hub 16, infusion catheter 10 is advanced distally through hemostatic port 33 and lumen 31 of emboli removal catheter 30. Infusion catheter 10 is guided distally via atraumatic tip 12 to the treatment site. With retrograde flow established in vessel V, atraumatic tip 12 is advanced distally through occlusion S, as shown in FIG. 3.

In an alternative method step, infusion catheter 10 may be guided through occlusion S using a guidewire and micro catheter (not shown). In this method step, after deploying occlusive element 32 of emboli removal catheter 32 and establishing retrograde flow in treatment vessel V, a conventional guidewire (not shown) then traverses occlusion S. A micro catheter (not shown), having an inner diameter larger than the outer diameter of infusion catheter 10, then is advanced over the guidewire through lumen 31 and through occlusion S. The guidewire then is removed from within the micro catheter, and infusion catheter 10 is advanced distally through the micro catheter to a location distal of the occlusion. The micro catheter is removed, leaving the infusion catheter positioned as shown in FIG. 3.

Although infusion catheter 10 preferably is constructed so that it comprises axial pushability characteristics similar to a conventional guidewire, removable stylet 19 optionally may be disposed within lumen 11 to further enhance pushability of infusion catheter 10. If removable stylet 19 is used, then the infusion means, e.g., tubing 18 of infusion pump 17, is coupled to proximal hub 16 after removable stylet 19 is removed from within lumen 11.

The distal end of infusion catheter 10 then preferably is positioned so that at least one delivery port 14 is disposed within occlusion S. Proximal and distal radiopaque markers 47 and 49, which are described hereinbelow with respect to FIG. 4, may be used to facilitate positioning of delivery port 14 within occlusion S. At this time, fluid 20 may be delivered to delivery port 14 at a desired pressure via infusion pump 17 coupled to lumen 11. Fluid 20 exits through delivery port 14, as shown in FIG. 3.

Infusion of fluid 20 dilutes and/or fragments occlusion S, which typically comprises a fibrin network in which red blood cells are trapped. The dilution of occlusion S is expected to alter the composition of occlusion S and provide a lubricious coating between the occlusion and the vessel wall. This reduces adhesion of occlusion S to the intima of vessel V, and eventually causes occlusion S to dislodge. Emboli E generated during the procedure will be directed toward emboli removal catheter 30 for removal due to the retrograde flow established.

In a preferred embodiment, delivery port 14 may comprise an angled taper, as shown in FIG. 4 hereinbelow, to infuse fluid 20 into occlusion S in a proximal direction, as shown in FIG. 3. Additionally, during the period in which fluid 20 is infused into occlusion S and emboli E are liberated, suction-assisted aspiration may be provided through lumen 31, e.g., using a syringe (not shown) coupled to the proximal end of emboli removal catheter 30, to assist in directing emboli E into lumen 31.

Infusion catheter 10 may be repositioned during the infusion of fluid 20 to target selected regions within occlusion S. Once occlusion S has been satisfactorily dislodged, infusion catheter 10 may be retracted proximally into lumen 31 of emboli removal catheter 30 and removed from the patient's vessel. Emboli removal catheter 30 may still provide retrograde flow in vessel V for a desired time thereafter, to ensure that all emboli E are removed. Upon completion of the procedure, occlusive element 32 is contracted and emboli removal catheter 30 is removed from the patient's vessel.

Referring now to FIG. 4, a side view of a distal end of an infusion catheter constructed in accordance with the present invention is described. Infusion catheter 40 having proximal and distal ends and lumen 41 extending therebetween comprises atraumatic tip 42 disposed at the distal end. Infusion catheter 40 is constructed in accordance with infusion catheter 10 of FIG. 1, except as noted below.

In FIG. 4, infusion catheter 40 comprises at least one delivery port 44 disposed proximal of atraumatic tip 42. Infusion catheter 40 further comprises at least one radiopaque marker band disposed proximal of atraumatic tip 42 to aid in positioning delivery port 44 within an occlusion. In a preferred embodiment, delivery port 44 is disposed between proximal radiopaque marker band 47 and distal radiopaque marker band 49. Proximal and distal radiopaque marker bands 47 and 49 may be used to define infusion segment 'x', which allows a physician to visualize the region in which delivery port 14 is disposed within an occlusion under fluoroscopy.

At least one delivery port 44 is disposed in a lateral wall of the infusion catheter to cause fluid infused into the occlusion to form a jet having a trajectory that forms an oblique angle relative to a longitudinal axis of the catheter. This orientation of delivery port 44 is referred to hereinafter as an "angled taper." The angled taper enhances the dilution of the occlusion and/or urges emboli in a proximal direction. In a preferred embodiment, at least one delivery port 44 comprises proximal taper 45, which causes fluid 50 to be infused in a proximal direction, as shown in FIG. 4. By causing fluid 50 to be infused into an occlusion in a proximal direction, emboli generated during the disruption of the occlusion may be urged in the proximal direction. It will be appreciated by those skilled in the art that while delivery port 44 is depicted as having a circular configuration in FIG. 4, delivery port 44 alternatively may comprise an elliptical shape or other configuration that may influence the infusion properties of fluid 50.

Figure 5:
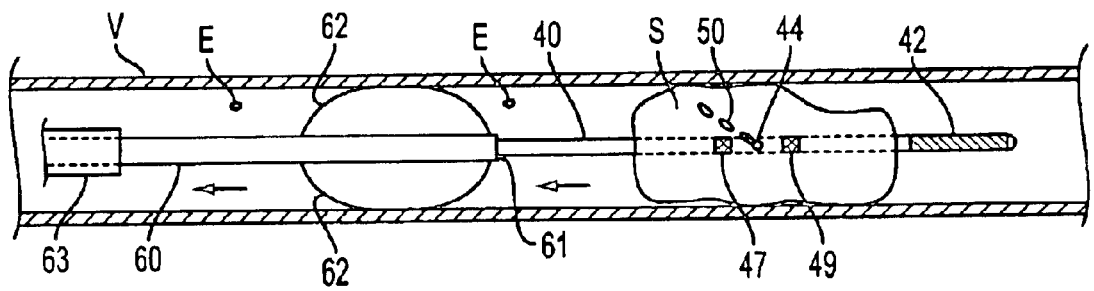
FIG. 5 provides a side sectional view of apparatus of the present invention used in conjunction with a centering device.

Referring now to FIG. 5, a side sectional view of a centering device that may be used in conjunction with an infusion catheter of the present invention is provided. Centering device 60, which has proximal and distal ends and lumen 61 extending therebetween, E comprises a plurality of deployable struts 62 disposed at the distal end, as shown in FIG. 5. Deployable struts 62 preferably are provided in a contracted state when constrained within outer sheath 63 having proximal and distal ends and a lumen extending therebetween. Deployable struts 62 preferably comprise a shape memory material, such as a Nickel-Titanium alloy, that causes deployable struts 62 to self-deploy to a predetermined shape when outer sheath 63 is retracted proximally. As shown from a cross-sectional view in FIG. 6, deployable struts 62 preferably are symmetrically disposed about centering device 60, and further are sized to engage the inner wall of treatment vessel V in the deployed state.

Centering device 60 preferably is used in conjunction with emboli removal catheter 30 and infusion catheter 40. In this embodiment, the outer diameter of outer sheath 63 is smaller than the inner diameter of lumen 31 of emboli removal catheter 30, while the inner diameter of lumen 61 of centering device 60 is larger than the outer diameter of infusion catheter 40.

In use, emboli removal catheter 30 is disposed in a patient's vessel proximal of an occlusion and retrograde flow is established through lumen 31, as described hereinabove with respect to FIG. 2. A guidewire (not shown) then is positioned at a location just proximal of occlusion S. Centering device 60, having deployable struts 62 provided in a contracted state within outer sheath 63, is advanced distally over the guidewire to a location just proximal of occlusion S. Outer sheath 63 then is retracted proximally to self-deploy deployable struts 62, as shown in FIG. 5. At this time, the guidewire is removed from within lumen 61 of centering device 60.

With centering device 60 deployed just proximal of occlusion S, infusion catheter 40 then is distally advanced through lumen 61 of centering device 60. Atraumatic tip 42 traverses occlusion S, guided by centering device 60, so that it crosses occlusion S along a central axis, as shown in FIG. 5. Removable stylet 19 of FIG. 1 optionally may be disposed within lumen 41 to enhance pushability of infusion catheter 40 during placement. Proximal and distal radiopaque marker bands 47 and 49 may be used to position delivery port 44 at a desired location within occlusion S.

At this time, fluid 50, which preferably comprises saline, may be delivered to delivery port 44 via lumen 41 and proximal hub 16 of FIG. 1, e.g., using tubing 18 of infusion pump 17 or, alternatively, a syringe (not shown). Angled taper 45 of delivery port 44 preferably causes fluid 50 to be infused into occlusion S in a proximal direction. As described hereinabove with respect to FIG. 3, the infusion of fluid dilutes the occlusion. The dilution of the occlusion may alter the composition of the occlusion and provide a lubricious coating between the occlusion and the vessel wall, which reduces adhesion of the occlusion to the intima of the vessel wall and causes the occlusion to dislodge. During the infusion process, centering device 60 serves to stabilize infusion catheter 40 in a central position within vessel V. The pressure at which fluid 50 is infused may be controlled or monitored by a physician, e.g., using pressure regulating device 17 of FIG. 1.

Figure 6:
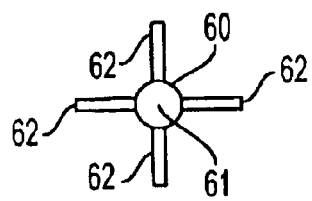
FIG. 6 provides a cross-sectional view of the distal end of the centering device of FIG. 5.

Any emboli E generated during the infusion of fluid 50 are directed in a retrograde fashion toward emboli removal catheter 30 due to the previously established retrograde flow. Because deployable struts 62 do not fully occlude the vessel when deployed, as shown in FIG. 6, retrograde blood flow and emboli E are directed past deployable struts 62 and toward emboli removal catheter 30.

When occlusion S has been satisfactorily disrupted, infusion catheter 40 may be retracted proximally through lumen 61 of centering device 60. A contrast agent may be delivered to the treatment site, e.g., via lumen 61, to check vessel patency under fluoroscopy. When patency is adequately restored, outer sheath 63 may be advanced distally over centering device 60 to collapse deployable struts 62 within sheath 63. Centering device 60 and outer sheath 63 then may be removed from the patient's vessel and, subsequently, emboli removal catheter 30 may be removed from the patient's vessel.

While preferred illustrative embodiments of the invention are described above, it will be apparent to one skilled in the art that various changes and modifications may be made therein without departing from the invention. The appended claims are intended to cover all such changes and modifications that fall within the true spirit and scope of the invention.

What is claimed is:

1. Apparatus suitable for disrupting a vascular occlusion adhered to a vessel wall, the apparatus comprising:

an infusion catheter having proximal and distal ends and a lumen extending therebetween, an atraumatic tip disposed at the distal end, and at least one delivery port disposed proximal of the atraumatic tip in fluid communication with the lumen, the at least one delivery port configured to infuse fluid into the occlusion so that the fluid reduces adhesion of the occlusion to an intima of the vessel wall;

an emboli removal catheter having a proximal end, a distal end including an occlusive element, and a lumen extending between the proximal and distal ends, the lumen sized to permit the longitudinal advancement of the infusion catheter therethrough; and a venous return sheath having proximal and distal ends and a lumen extending therebetween, the venous return sheath in fluid communication with the lumen of the emboli removal catheter and is adapted to be disposed in a patient's venous system.

2. The apparatus of claim 1 wherein the atraumatic tip comprises a platinum coil.

3. The apparatus of claim 1 wherein at least one delivery port delivers a jet of fluid that forms an oblique angle relative to a longitudinal axis of the infusion catheter.

4. The apparatus of claim 3 wherein the delivery port causes fluid to be ejected in a proximal direction.

5. The apparatus of claim 1 wherein the delivery port comprises a circular configuration.

6. The apparatus of claim 1 wherein the infusion catheter further comprises at least one radiopaque marker band disposed proximal of the atraumatic tip.

7. The apparatus of claim 6 wherein a first radiopaque marker band is disposed proximal of the delivery port and a second radiopaque marker band is disposed distal of the delivery port.

8. The apparatus of claim 1 wherein the fluid is saline.

9. The apparatus of claim 1 further comprising a removable stylet that is configured to be longitudinally advanced within the lumen of infusion catheter.

10. The apparatus of claim 1 further comprising an infusion pump configured to regulate the flow of fluid infused into the lumen of the infusion catheter.

11. The apparatus of claim 1 wherein the fluid is a drug.

12. The apparatus of claim 1 further comprising a valve disposed between the emboli removal catheter and the venous return sheath, wherein the valve is configured to selectively inhibit fluid communication between the lumen of the emboli removal catheter and the lumen of the venous return sheath.

13. The apparatus of claim 1 further comprising a filter disposed between the emboli removal catheter and the venous return sheath.

14. Apparatus suitable for treating an occlusion adhered to a vessel wall, the apparatus comprising:
an infusion catheter having proximal and distal ends and a lumen extending therebetween, an atraumatic tip disposed at the distal end, and at least one delivery port disposed proximal of the atraumatic tip in fluid communication with the lumen; and
a centering device having proximal and distal ends and a lumen extending therebetween, the centering device comprising a plurality of deployable struts disposed at the distal end, the lumen adapted to permit the infusion catheter to pass therethrough,
wherein the infusion catheter is configured to infuse fluid into the occlusion so that the fluid reduces adhesion of the occlusion to an intima of the vessel wall.

15. The apparatus of claim 14 further comprising an outer sheath having proximal and distal ends and a lumen extending therebetween, the outer sheath being configured to constrain the deployable struts in a contracted state within the outer sheath.

16. The apparatus of claim 14 wherein the deployable struts are sized to engage the vessel wall in a deployed state.

17. The apparatus of 14 wherein the deployable struts comprise a nickel-titanium alloy.

18. The apparatus of claim 14 wherein at least one delivery port delivers a jet of fluid that forms an oblique angle relative to a longitudinal axis of the infusion catheter.

19. The apparatus of claim 18 wherein the delivery port causes fluid to be ejected in a proximal direction.

20. The apparatus of claim 14 wherein the infusion catheter further comprises at least one radiopaque marker band disposed proximal of the atraumatic tip.

21. The apparatus of claim 20 wherein a first radiopaque marker band is disposed proximal of the delivery port and a second radiopaque marker band is disposed distal of the delivery port.

22. The apparatus of claim 14 further comprising an emboli removal catheter having proximal and distal ends and a lumen extending therebetween, and further comprising an occlusive element disposed at the distal end, wherein the lumen of the emboli removal catheter is sized to permit the longitudinal advancement of the centering device.

23. A method for treating an occlusion adhered to a vessel wall, the method comprising:
providing an infusion catheter having proximal and distal ends, a lumen extending therebetween, an atraumatic tip disposed at the distal end, and at least one delivery port disposed proximal of the atraumatic tip in fluid communication with the lumen;
providing a centering device having proximal and distal ends, a lumen extending therebetween, and a plurality of deployable struts disposed at the distal end in a contracted state;
positioning the centering device at a location proximal of the occlusion;
deploying the plurality of deployable struts; and
advancing the infusion catheter through the lumen of the centering device to advance the atraumatic tip through the occlusion;
positioning the delivery port at a desired location within the occlusion; and
infusing fluid into the occlusion via the delivery port so that the fluid reduces adhesion of the occlusion to an intima of the vessel wall.

24. The method of claim 23 wherein positioning the delivery port at a desired location within the occlusion comprises:
providing at least one radiopaque marker band disposed on the infusion catheter at a location proximal of the atraumatic tip; and
using the radiopaque marker band to determine the position of the delivery port within the occlusion.

25. The method of claim 23 wherein fluid is infused into the occlusion at a controlled rate using an infusion pump.

26. The method of claim 23 further comprising:
providing an emboli removal catheter having proximal and distal ends and a lumen extending therebetween, and further comprising an occlusive element disposed at the distal end, wherein the lumen of the emboli removal catheter is sized to permit the longitudinal advancement of the infusion catheter;
deploying the occlusive element at a position proximal of the centering device to occlude antegrade flow in a vessel;
establishing retrograde flow through the lumen of the emboli removal catheter to influence flow characteristics in a treatment vessel; and
causing emboli generated during the infusion of fluid into the occlusion to be directed into the emboli removal catheter.

27. The method of claim 23 wherein fluid is infused into the occlusion in a proximal direction.

28. The method of claim 23 wherein deploying the plurality of deployable struts comprises proximally retracting an outer sheath that is used to constrain the deployable struts in the contracted state.

29. A method for treating an occlusion adhered to a wall of a patient's vessel, the method comprising:

providing an emboli removal system having a proximal end adapted to be inserted in a patient's venous system, distal end including an occlusive element, and a lumen extending between the proximal and distal ends;

providing an infusion catheter having proximal and distal ends, a lumen extending therebetween, an atraumatic tip disposed at the distal end, and at least one delivery port disposed proximal of the atraumatic tip in fluid communication with the lumen;

advancing the distal end of the emboli removal system through the vessel to a position proximal of the occlusion;

deploying the occlusion element to occlude antegrade flow through the vessel;

inserting the proximal end of the emboli removal system into the patient's venous system;

advancing the infusion catheter so that the atraumatic tip penetrates the occlusion;

positioning the delivery port at a desired location within the occlusion;

infusing fluid into the occlusion via the delivery port to reduce adhesion of the occlusion to an intima of the vessel wall, dislodge the occlusion and generate emboli;

aspirating emboli-laden blood through the emboli removal system;

filtering emboli-laden blood aspirated through from the vessel to remove emboli; and re-infusing filtered blood into the patient's venous system.

30. The method of claim 29 wherein positioning the delivery port at a desired location within the occlusion comprises:

providing at least one radiopaque marker band disposed on the infusion catheter adjacent to the delivery port; and using the radiopaque marker band to determine the position of the delivery port within the occlusion.

31. The method of claim 29 wherein infusing fluid into the occlusion further comprises infusing fluid into the occlusion at a controlled rate using an infusion pump.

32. The method of claim 29 further comprising, prior to advancing the infusion catheter, establishing retrograde flow through the vessel.

33. The method of claim 29 wherein infusing fluid into the occlusion further comprises infusing fluid into the occlusion in a proximal direction.

34. The method of claim 29 further comprising:

providing a centering device having proximal and distal ends, a lumen extending therebetween, and a plurality of deployable struts disposed at the distal end in a contracted state;

prior to advancing the infusion catheter, inserting the centering device through the lumen of the emboli removal system to position the centering device at a location proximal of the occlusion and distal of the occlusive element;

deploying the plurality of deployable struts; and wherein advancing the infusion catheter comprises advancing the infusion catheter through the lumen of the centering device.

35. The method of claim 34 wherein deploying the plurality of deployable struts comprises proximally retracting an outer sheath that is used to constrain the deployable struts in the contracted state.

* * * * *